United States Patent [19]
Marsden

[11] Patent Number: 5,965,357
[45] Date of Patent: Oct. 12, 1999

[54] PEPTIDES STRUCTURES AND THEIR USE IN DIAGNOSIS OF HERPES SIMPLEX VIRUS TYPE 2

[75] Inventor: Howard Sinkinson Marsden, Glasgow, United Kingdom

[73] Assignee: Medical Research Council, London, United Kingdom

[21] Appl. No.: 09/017,205

[22] Filed: Feb. 2, 1998

[51] Int. Cl.$^6$ ...................................................... C12Q 1/70
[52] U.S. Cl. ................................ 435/5; 435/7.1; 435/7.9; 435/7.91; 435/7.92; 435/7.93; 435/7.94; 435/7.95; 435/975; 436/518; 530/326; 530/327; 530/826
[58] Field of Search ......................... 435/5, 7.1, 7.9–7.95, 435/975; 436/518; 530/326, 327, 826

[56] References Cited

U.S. PATENT DOCUMENTS 5,229,490  7/1993  Tam ......................................... 530/324

FOREIGN PATENT DOCUMENTS

WO 96/32962  10/1996  WIPO .
WO 98/03543  1/1998  WIPO .
WO 98/03544  1/1998  WIPO .

OTHER PUBLICATIONS

J–A. Liljeqvist et al., "Localization of Type–Specific Epitopes in Herpes Simplex Type 2 Glycoprotein G by Human Antibodies", 22$^{nd}$ Herpesvirus Workshop, University of California, La Jolla, San Diego, Aug. 2–8 1997, Abstract N°125.
J–A. Liljeqvist et al., "Definition of an Antigenic Site of Herpes Simplex Type 2 Glycoprotein G by Monoclonal Antibodies", 21$^{st}$ Herpesvirus Workshop, Northern Illinois University, Chicago, Jul. 27–Aug. 2, 1996, Abstract N°431.
J–A. Liljeqvist et al., "Definition of an Antigenic Site of Herpes Simplex Type 2 Glycoprotein G by Monoclonal Antibodies", 21$^{st}$ Herpesvirus Workshop, Northern Illinois University, Chicago, Jul. 27–Aug. 2, 1996, Photographs taken of a displayed poster.
A. Grabowskwa et al., "Identification of type–specific epitopes of the glycoprotein G of HSV–2 using a phage peptide display library", 21$^{st}$ Herpesvirus Workshop, Northern Illinois University, Chicago, Jul. 27–Aug. 2, 1996, Abstract N°136.
A. Grabowskwa et al., "Identification of type–specific epitopes of the glycoprotein G of HSV–2 using a phage peptide display library", 21$^{st}$ Herpesvirus Workshop, Northern Illinois University, Chicago, Jul. 27–Aug. 2, 1996, Photographs taken of a displayed poster.
M. Levi et al., Peptide Sequences of Glycoprotein G–2 Discriminate between Herpes Simplex Virus Type 2 (HSV–2) and HSV–1 Antibodies, Clinical and Diagnostic Laboratory Immunology, 3, 265–269 (1996).
J. P. Tam, "Synthetic peptide vaccine design: Synthesis and properties of a high–density multiple antigenic peptide system", Proc. Natl. Acad. Sci. USA, 85, 5409–5413 (1988).
H. S. Marsden et al., "Physical Mapping of Herpes Simplex Virus–Induced Polypeptides", J. Virology 28, 624–642 (1978).
H. S. Marsden et al., "Characterization of the 92,000–Dalton Glycoprotein Induced by Herpes Simplex Virus Type 2", J. Virology 50, 547–554 (1984).
B. Roizman et al., "Identification and Preliminary Mapping with Monoclonal Antibodies of a Herpes Simplex Virus 2 Glycoprotein Lacking a Known Type 1 Counterpart", Virology 133, 242–247 (1984).
M. C. Frame et al., "Novel Herpes Simplex Virus Type 1 Glycoproteins Identified by Antiserum against a Synthetic Oligopeptide from the Predicted Product of Gene US4", J. gen. Virol. 67, 745–751 (1986).
M. Ackermann et al., "Identification, Properties, and Gene Location of a Novel Glycoprotein Specified by Herpes Simplex Virus 1 ", Virology 150, 207–220 (1986).
D. J. McGeoch et al., "DNA Sequence and Genetic Content of HindIII 1 Region in the Short Unique Component of the Herpes Simplex Virus Type 2 Genome: Identification of the Gene Encoding Glycoprotein G, and Evolutionary Comparisons", J. gen. Virol. 68, 19–38 (1987).
World Health Organisation, Regional Office for Europe, "Epidemiology of Herpes Simplex Virus Infections and Surveillance of other STDs in Europe", Report on a Workshop, Copenhagen 19–20 Jun. 1995.
Liljeqvist et al., "Localization of type–specific epitodes of herpes simplex . . . ," Journal of General Virology, vol. 79, pp. 1215–1224 (1998).

Primary Examiner—Jeffrey Stucker
Attorney, Agent, or Firm—Nixon & Vanderhye

[57]  ABSTRACT

A multiply-displayed peptide structure is provided for the serodiagnosis of HSV-2 antibodies, preferably by ELISA. The structure has the formula (1)): $[(X^1)_p$—16aa sequence—$(X^2)_q$—Sp$]_n$—core, wherein "16aa sequence" represents a sequence (SEQ ID NO: 68)

```
Glu Glu Phe Glu Gly Ala Gly Asp Gly Glu Pro Pro
 1               5                   10
                                    Glu Asp Asp Asp
                                             15
```

$X^1$ and $X^2$ which may be the same or different represent from 1 to 6 non-interfering amino acid residues, which may be the same or different;
Sp represents a spacer group extending outwardly from the core;

n is at least 4;

p is 0 or 1;

q is 0 or 1;
and the linkage between the core and the spacer group may be chemical or physical.
Preferably p is 1, q is 1, $X^1$ is Pro, n is 4, and the core is a branched lysine core, whereby the whole structure is a peptide. The monomeric peptides $(X^1)_p$—16aa sequence—$(X^2)_q$—(Sp)$_r$, where r is 0 or 1 and their functional derivatives are useful intermediates in preparing the above structures.

14 Claims, 2 Drawing Sheets

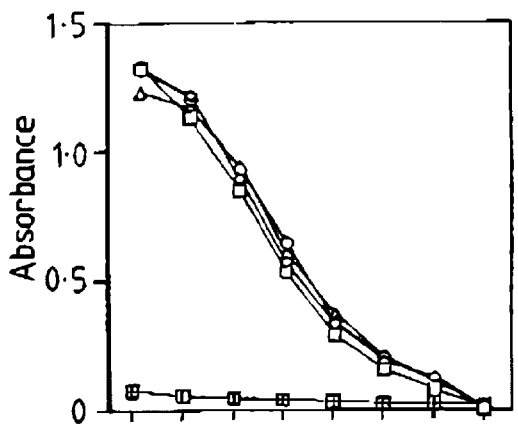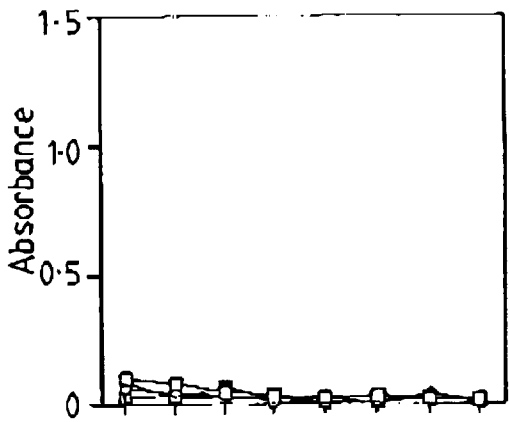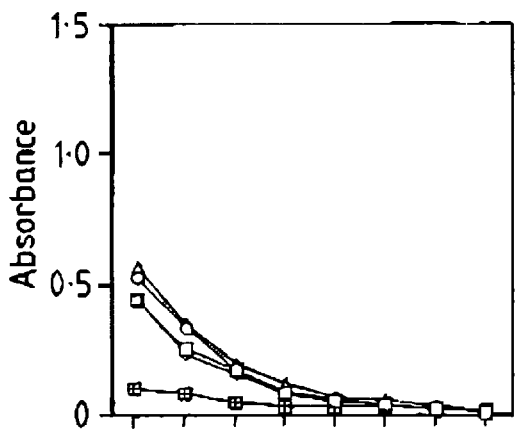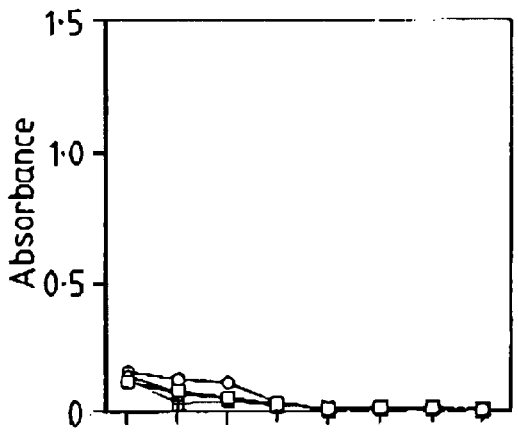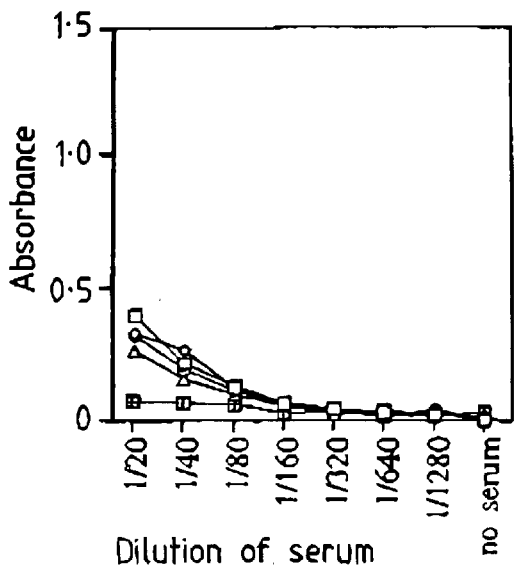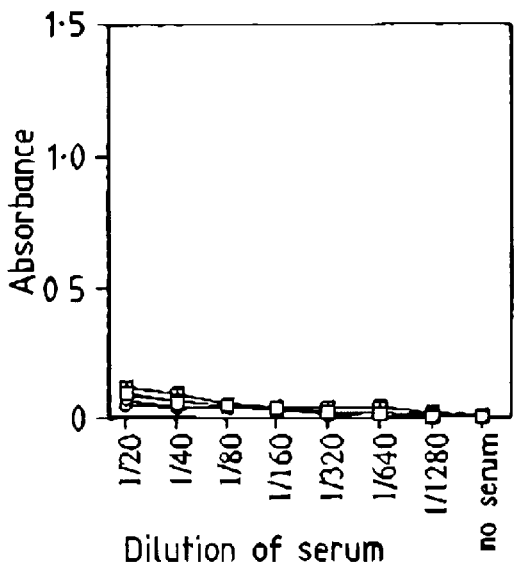

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:1:

Arg Gly Gly Ser Gly Val Pro Gly Pro Ile Asn Pro Pro Asn Ser Asp
   1              5                   10               15

Val Val (2) INFORMATION FOR SEQ ID NO:2:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:2:

Asn Pro Pro Asn Ser Asp Val Val Phe Pro Gly Gly Ser Pro Val Ala
   1              5                   10               15

Gln Tyr (2) INFORMATION FOR SEQ ID NO:3:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:3:

```
Gly Gly Ser Pro Val Ala Gln Tyr Cys Tyr Ala Tyr Pro Arg Leu Asp
1               5                   10                  15

Asp Pro
```

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:4:

```
Ala Tyr Pro Arg Leu Asp Asp Pro Gly Pro Leu Gly Ser Ala Asp Ala
1               5                   10                  15

Gly Arg
```

(2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:5:

```
Leu Gly Ser Ala Asp Ala Gly Arg Gln Asp Leu Pro Arg Arg Val Val
1               5                   10                  15

Arg His
```

(2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:6:

```
Leu Pro Arg Arg Val Val Arg His Glu Pro Leu Gly Arg Ser Phe Leu
1               5                   10                  15

Thr Gly
```

(2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:7:

Leu Gly Arg Ser Phe Leu Thr Gly Gly Leu Val Leu Leu Ala Pro Pro
1               5                   10                  15

Val Arg (2) INFORMATION FOR SEQ ID NO:8:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:8:

Val Leu Leu Ala Pro Pro Val Arg Gly Phe Gly Ala Pro Asn Ala Thr
1               5                   10                  15

Tyr Ala (2) INFORMATION FOR SEQ ID NO:9:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:9:

Gly Ala Pro Asn Ala Thr Tyr Ala Ala Arg Val Thr Tyr Tyr Arg Leu
1               5                   10                  15

Thr Arg (2) INFORMATION FOR SEQ ID NO:10:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:10:

Val Thr Tyr Tyr Arg Leu Thr Arg Ala Cys Arg Gln Pro Ile Leu Leu
1               5                   10                  15

Arg Gln (2) INFORMATION FOR SEQ ID NO:11:

(i) SEQUENCE CHARACTERISTICS:
      (A) LENGTH: 18 amino acids
      (B) TYPE: amino acid
      (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:11:

Arg Gln Pro Ile Leu Leu Arg Gln Tyr Gly Gly Cys Arg Gly Gly Glu

```
                    1               5              10             15

Pro Pro (2) INFORMATION FOR SEQ ID NO:12:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:12:

Gly Cys Arg Gly Gly Glu Pro Pro Ser Pro Lys Thr Cys Gly Ser Tyr
    1               5                   10                  15

Thr Tyr (2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:13:

Lys Thr Cys Gly Ser Tyr Thr Tyr Thr Tyr Gln Gly Gly Gly Pro Pro
    1               5                   10                  15

Thr Arg (2) INFORMATION FOR SEQ ID NO:14:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:14:

Gln Gly Gly Gly Pro Pro Thr Arg Tyr Ala Leu Val Asn Ala Ser Leu
    1               5                   10                  15

Leu Val (2) INFORMATION FOR SEQ ID NO:15:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:15:

Leu Val Asn Ala Ser Leu Leu Val Pro Ile Trp Asp Arg Ala Ala Glu
    1               5                   10                  15

Thr Phe
```

-continued (2) INFORMATION FOR SEQ ID NO:16:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:16:

```
Trp Asp Arg Ala Ala Glu Thr Phe Glu Tyr Gln Ile Glu Leu Gly Gly
1               5                  10                  15
Glu Leu
```

(2) INFORMATION FOR SEQ ID NO:17:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:17:

```
Gln Ile Glu Leu Gly Gly Glu Leu His Val Gly Leu Leu Trp Val Glu
1               5                  10                  15
Val Gly
```

(2) INFORMATION FOR SEQ ID NO:18:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:18:

```
Gly Leu Leu Trp Val Glu Val Gly Gly Glu Gly Pro Gly Pro Thr Ala
1               5                  10                  15
Pro Pro
```

(2) INFORMATION FOR SEQ ID NO:19:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:19:

```
Gly Pro Gly Pro Thr Ala Pro Pro Gln Ala Ala Arg Ala Glu Gly Gly
1               5                  10                  15
Pro Cys
```

(2) INFORMATION FOR SEQ ID NO:20:

(i) SEQUENCE CHARACTERISTICS:

```
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:20:

Ala Arg Ala Glu Gly Gly Pro Cys Val Pro Pro Val Pro Ala Gly Arg
    1               5                   10                  15

Pro Trp (2) INFORMATION FOR SEQ ID NO:21:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:21:

Pro Val Pro Ala Gly Arg Pro Trp Arg Ser Val Pro Pro Val Trp Tyr
    1               5                   10                  15

Ser Ala (2) INFORMATION FOR SEQ ID NO:22:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:22:

Val Pro Pro Val Trp Tyr Ser Ala Pro Asn Pro Gly Phe Arg Gly Leu
    1               5                   10                  15

Arg Phe (2) INFORMATION FOR SEQ ID NO:23:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:23:

Pro Gly Phe Arg Gly Leu Arg Phe Arg Glu Arg Cys Leu Pro Pro Gln
    1               5                   10                  15

Thr Pro (2) INFORMATION FOR SEQ ID NO:24:

(i) SEQUENCE CHARACTERISTICS:
        (A) LENGTH: 18 amino acids
        (B) TYPE: amino acid
        (D) TOPOLOGY: linear
```

(ii) MOLECULE TYPE: peptide from HSV-2 glycoprotein G (v) FRAGMENT TYPE: internal (xi) SEQUENCE DESCRIPTION: SEQ ID NO:24:

```
Arg Cys Leu Pro Pro Gln Thr Pro Ala Ala Pro Ser Asp Leu Pro Arg
1               5                   10                  15

Val Ala
```

(2) INFORMATION FOR SEQ ID NO:25:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:25:

```
Pro Ser Asp Leu Pro Arg Val Ala Phe Ala Pro Gln Ser Leu Leu Val
1               5                   10                  15

Gly Ile
```

(2) INFORMATION FOR SEQ ID NO:26:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:26:

```
Pro Gln Ser Leu Leu Val Gly Ile Thr Gly Arg Thr Phe Ile Arg Met
1               5                   10                  15

Ala Arg
```

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:27:

```
Arg Thr Phe Ile Arg Met Ala Arg Pro Thr Glu Asp Val Gly Val Leu
1               5                   10                  15

Pro Pro
```

(2) INFORMATION FOR SEQ ID NO:28:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:28:

Glu Asp Val Gly Val Leu Pro Pro His Trp Ala Pro Gly Ala Leu Asp
    1               5                   10                  15

Asp Gly (2) INFORMATION FOR SEQ ID NO:29:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:29:

Ala Pro Gly Ala Leu Asp Asp Gly Pro Tyr Ala Pro Phe Pro Pro Arg
    1               5                   10                  15

Pro Arg (2) INFORMATION FOR SEQ ID NO:30:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:30:

Ala Pro Phe Pro Pro Arg Pro Arg Phe Arg Arg Ala Leu Arg Thr Asp
    1               5                   10                  15

Pro Glu (2) INFORMATION FOR SEQ ID NO:31:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:31:

Arg Ala Leu Arg Thr Asp Pro Glu Gly Val Asp Pro Asp Val Arg Ala
    1               5                   10                  15

Pro Arg (2) INFORMATION FOR SEQ ID NO:32:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:32:

Asp Pro Asp Val Arg Ala Pro Arg Thr Gly Arg Arg Leu Met Ala Leu
    1               5                   10                  15

Thr Glu (2) INFORMATION FOR SEQ ID NO:33:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:33:

Arg Arg Leu Met Ala Leu Thr Glu Asp Thr Ser Ser Asp Ser Pro Thr
    1               5                   10                  15

Ser Ala (2) INFORMATION FOR SEQ ID NO:34:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:34:

Ser Ser Asp Ser Pro Thr Ser Ala Pro Glu Lys Thr Pro Leu Pro Val
    1               5                   10                  15

Ser Ala (2) INFORMATION FOR SEQ ID NO:35:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:35:

Lys Thr Pro Leu Pro Val Ser Ala Thr Ala Met Ala Pro Ser Val Asp
    1               5                   10                  15

Pro Ser (2) INFORMATION FOR SEQ ID NO:36:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:36:

Met Ala Pro Ser Val Asp Pro Ser Ala Glu Pro Thr Ala Pro Ala Thr
    1               5                   10                  15

Thr Thr (2) INFORMATION FOR SEQ ID NO:37:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:37:

```
Pro Thr Ala Pro Ala Thr Thr Thr Pro Pro Asp Glu Met Ala Thr Gln
1               5                   10                  15

Ala Ala
```

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:38:

```
Asp Glu Met Ala Thr Gln Ala Ala Thr Val Ala Val Thr Pro Glu Glu
1               5                   10                  15

Thr Ala
```

(2) INFORMATION FOR SEQ ID NO:39:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:39:

```
Ala Val Thr Pro Glu Glu Thr Ala Val Ala Ser Pro Pro Ala Thr Ala
1               5                   10                  15

Ser Val
```

(2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:40:

```
Ser Pro Pro Ala Thr Ala Ser Val Glu Ser Ser Pro Leu Pro Ala Ala
1               5                   10                  15

Ala Ala
```

(2) INFORMATION FOR SEQ ID NO:41:

(i) SEQUENCE CHARACTERISTICS:
        (A) LENGTH: 18 amino acids

```
          (B) TYPE: amino acid
          (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:41:

Ser Pro Leu Pro Ala Ala Ala Ala Thr Pro Gly Ala Gly His Thr
    1               5                   10                  15

Asn Thr (2) INFORMATION FOR SEQ ID NO:42:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:42:

Pro Gly Ala Gly His Thr Asn Thr Ser Ser Ala Ser Ala Ala Lys Thr
    1               5                   10                  15

Pro Pro (2) INFORMATION FOR SEQ ID NO:43:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:43:

Ala Ser Ala Ala Lys Thr Pro Pro Thr Thr Pro Ala Pro Thr Thr Pro
    1               5                   10                  15

Pro Pro (2) INFORMATION FOR SEQ ID NO:44:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:44:

Pro Ala Pro Thr Thr Pro Pro Thr Ser Thr His Ala Thr Pro Arg
    1               5                   10                  15

Pro Thr (2) INFORMATION FOR SEQ ID NO:45:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G
```

-continued (v) FRAGMENT TYPE: internal (xi) SEQUENCE DESCRIPTION: SEQ ID NO:45:

Thr His Ala Thr Pro Arg Pro Thr Thr Pro Gly Pro Gln Thr Thr Pro
   1               5                  10                  15

Pro Gly (2) INFORMATION FOR SEQ ID NO:46:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:46:

Gly Pro Gln Thr Thr Pro Pro Gly Pro Ala Thr Pro Gly Pro Val Gly
   1               5                  10                  15

Ala Ser (2) INFORMATION FOR SEQ ID NO:47:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:47:

Thr Pro Gly Pro Val Gly Ala Ser Ala Ala Pro Thr Ala Asp Ser Pro
   1               5                  10                  15

Leu Thr (2) INFORMATION FOR SEQ ID NO:48:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:48:

Pro Thr Ala Asp Ser Pro Leu Thr Ala Ser Pro Pro Ala Thr Ala Pro
   1               5                  10                  15

Gly Pro (2) INFORMATION FOR SEQ ID NO:49:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:49:

```
     Pro Pro Ala Thr Ala Pro Gly Pro Ser Ala Ala Asn Val Ser Val Ala
     1               5                   10                  15

Ala Thr
```

(2) INFORMATION FOR SEQ ID NO:50:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:50:

```
     Ala Asn Val Ser Val Ala Ala Thr Thr Ala Thr Pro Gly Thr Arg Gly
     1               5                   10                  15

Thr Ala
```

(2) INFORMATION FOR SEQ ID NO:51:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:51:

```
     Thr Pro Gly Thr Arg Gly Thr Ala Arg Thr Pro Pro Thr Asp Pro Lys
     1               5                   10                  15

Thr His
```

(2) INFORMATION FOR SEQ ID NO:52:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:52:

```
     Pro Pro Thr Asp Pro Lys Thr His Pro His Gly Pro Ala Asp Ala Pro
     1               5                   10                  15

Pro Gly
```

(2) INFORMATION FOR SEQ ID NO:53:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:53:

```
     Gly Pro Ala Asp Ala Pro Pro Gly Ser Pro Ala Pro Pro Pro Pro Glu
     1               5                   10                  15
```

His Arg (2) INFORMATION FOR SEQ ID NO:54:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:54:

Ala Pro Pro Pro Pro Glu His Arg Gly Gly Pro Glu Glu Phe Glu Gly
   1               5                   10                  15

Ala Gly (2) INFORMATION FOR SEQ ID NO:55:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:55:

Pro Glu Glu Phe Glu Gly Ala Gly Asp Gly Glu Pro Pro Glu Asp Asp
   1               5                   10                  15

Asp Ser (2) INFORMATION FOR SEQ ID NO:56:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:56:

Glu Pro Pro Glu Asp Asp Asp Ser Ala Thr Gly Leu Ala Phe Arg Thr
   1               5                   10                  15

Pro Asn (2) INFORMATION FOR SEQ ID NO:57:

(i) SEQUENCE CHARACTERISTICS:
       (A) LENGTH: 18 amino acids
       (B) TYPE: amino acid
       (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:57:

Gly Leu Ala Phe Arg Thr Pro Asn Pro Asn Lys Pro Pro Pro Ala Arg
   1               5                   10                  15

Pro Gly (2) INFORMATION FOR SEQ ID NO:58:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:58:

Lys Pro Pro Pro Ala Arg Pro Gly Pro Ile Arg Pro Thr Leu Pro Pro
   1               5                   10                  15

Gly Ile (2) INFORMATION FOR SEQ ID NO:59:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:59:

Arg Pro Thr Leu Pro Pro Gly Ile Leu Gly Pro Leu Ala Pro Asn Thr
   1               5                   10                  15

Pro Arg (2) INFORMATION FOR SEQ ID NO:60:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:60:

Pro Leu Ala Pro Asn Thr Pro Arg Pro Pro Ala Gln Ala Pro Ala Lys
   1               5                   10                  15

Asp Met (2) INFORMATION FOR SEQ ID NO:61:

(i) SEQUENCE CHARACTERISTICS:
         (A) LENGTH: 18 amino acids
         (B) TYPE: amino acid
         (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:61:

Ala Gln Ala Pro Ala Lys Asp Met Pro Ser Gly Pro Thr Pro Gly His
   1               5                   10                  15

Ile Pro (2) INFORMATION FOR SEQ ID NO:62:

(i) SEQUENCE CHARACTERISTICS:
         (A) LENGTH: 18 amino acids
         (B) TYPE: amino acid (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:62:

Gly Pro Thr Pro Gln His Ile Pro Leu Phe Trp Phe Leu Thr Ala Ser
    1               5                  10                  15

Pro Ala (2) INFORMATION FOR SEQ ID NO:63:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:63:

Trp Phe Leu Thr Ala Ser Pro Ala Leu Asp Ile Leu Phe Ile Ile Ser
    1               5                  10                  15

Thr Thr (2) INFORMATION FOR SEQ ID NO:64:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:64:

Ile Leu Phe Ile Ile Ser Thr Thr Leu His Thr Ala Ala Phe Val Cys
    1               5                  10                  15

Leu Val (2) INFORMATION FOR SEQ ID NO:65:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:65:

Thr Ala Ala Phe Val Cys Leu Val Ala Leu Ala Ala Gln Leu Trp Arg
    1               5                  10                  15

Gly Arg (2) INFORMATION FOR SEQ ID NO:66:

(i) SEQUENCE CHARACTERISTICS:
        (A) LENGTH: 18 amino acids
        (B) TYPE: amino acid
        (D) TOPOLOGY: linear (ii) MOLECULE TYPE: peptide from HSV-2 glycoprotein G -continued (v) FRAGMENT TYPE: internal (xi) SEQUENCE DESCRIPTION: SEQ ID NO:66:

Ala Ala Gln Leu Trp Arg Gly Arg Ala Gly Arg Arg Arg Tyr Ala His
    1               5                   10                  15

Pro Ser (2) INFORMATION FOR SEQ ID NO:67:

(i) SEQUENCE CHARACTERISTICS:
        (A) LENGTH: 19 amino acids
        (B) TYPE: amino acid
        (D) TOPOLOGY: linear (ii) MOLECULE TYPE: peptide from HSV-2 glycoprotein G (v) FRAGMENT TYPE: C-terminal (xi) SEQUENCE DESCRIPTION: SEQ ID NO:67:

Arg Arg Arg Tyr Ala His Pro Ser Val Arg Tyr Val Cys Leu Pro Pro
    1               5                   10                  15

Glu Arg Asp (2) INFORMATION FOR SEQ ID NO:68:

(i) SEQUENCE CHARACTERISTICS:
        (A) LENGTH: 16 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:68:

Glu Glu Phe Glu Gly Ala Gly Asp Gly Glu Pro Pro Glu Asp Asp Asp
    1               5                   10                  15

(2) INFORMATION FOR SEQ ID NO:69:

(i) SEQUENCE CHARACTERISTICS:
        (A) LENGTH: 6 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:69:

Glu His Arg Gly Gly Pro
    1               5

(2) INFORMATION FOR SEQ ID NO:70:

(i) SEQUENCE CHARACTERISTICS:
        (A) LENGTH: 5 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:70:

His Arg Gly Gly Pro
    1               5

(2) INFORMATION FOR SEQ ID NO:71:

(i) SEQUENCE CHARACTERISTICS:
        (A) LENGTH: 4 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:71:

Arg Gly Gly Pro
    1

(2) INFORMATION FOR SEQ ID NO:72:

(i) SEQUENCE CHARACTERISTICS:
        (A) LENGTH: 6 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:72:

Ser Ala Thr Gly Leu Phe
    1               5

(2) INFORMATION FOR SEQ ID NO:73:

(i) SEQUENCE CHARACTERISTICS:
        (A) LENGTH: 5 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:73:

Ser Ala Thr Gly Leu
    1               5

(2) INFORMATION FOR SEQ ID NO:74:

(i) SEQUENCE CHARACTERISTICS:
        (A) LENGTH: 4 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:74:

Ser Ala Thr Gly
    1

(2) INFORMATION FOR SEQ ID NO:75:

(i) SEQUENCE CHARACTERISTICS:
        (A) LENGTH: 17 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:75:

```
        Pro Glu Glu Phe Glu Gly Ala Gly Asp Gly Glu Pro Pro Glu Asp Asp
        1               5                   10                  15

Asp (2) INFORMATION FOR SEQ ID NO:76:

(i) SEQUENCE CHARACTERISTICS:
          (A) LENGTH: 17 amino acids
          (B) TYPE: amino acid
          (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:76:

Glu Glu Phe Glu Gly Ala Gly Asp Gly Glu Pro Pro Glu Asp Asp Asp
        1               5                   10                  15

Ser (2) INFORMATION FOR SEQ ID NO:77:

(i) SEQUENCE CHARACTERISTICS:
          (A) LENGTH: 20 amino acids
          (B) TYPE: amino acid
          (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:77:

Gly Gly Pro Glu Glu Phe Glu Gly Ala Gly Asp Gly Glu Pro Pro Glu
        1               5                   10                  15

Asp Asp Asp Ser
                20

(2) INFORMATION FOR SEQ ID NO:78:

(i) SEQUENCE CHARACTERISTICS:
          (A) LENGTH: 20 amino acids
          (B) TYPE: amino acid
          (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:78:

Pro Glu Glu Phe Glu Gly Ala Gly Asp Gly Glu Pro Pro Glu Asp Asp
        1               5                   10                  15

Asp Ser Ala Thr
                20

(2) INFORMATION FOR SEQ ID NO:79:

(i) SEQUENCE CHARACTERISTICS:
          (A) LENGTH: 22 amino acids
          (B) TYPE: amino acid
          (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:79:

Gly Gly Pro Glu Glu Phe Glu Gly Ala Gly Asp Gly Glu Pro Pro Glu
```

```
            1               5              10              15
        Asp Asp Asp Ser Ala Thr
        20

(2) INFORMATION FOR SEQ ID NO:80:

(i) SEQUENCE CHARACTERISTICS:
        (A) LENGTH: 22 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:80:

His Arg Gly Gly Pro Glu Glu Phe Glu Gly Ala Gly Asp Gly Glu Pro
        1               5                  10                  15

Pro Glu Asp Asp Asp Ser
        20

(2) INFORMATION FOR SEQ ID NO:81:

(i) SEQUENCE CHARACTERISTICS:
        (A) LENGTH: 22 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:81:

Pro Glu Glu Phe Glu Gly Ala Gly Asp Gly Glu Pro Pro Glu Asp Asp
        1               5                  10                  15

Asp Ser Ala Thr Gly Leu
        20

(2) INFORMATION FOR SEQ ID NO:82:

(i) SEQUENCE CHARACTERISTICS:
        (A) LENGTH: 26 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:82:

His Arg Gly Gly Pro Glu Glu Phe Glu Gly Ala Gly Asp Gly Glu Pro
        1               5                  10                  15

Pro Glu Asp Asp Asp Ser Ala Thr Gly Leu
        20                  25

(2) INFORMATION FOR SEQ ID NO:83:

(i) SEQUENCE CHARACTERISTICS:
        (A) LENGTH: 23 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:83:

Glu His Arg Gly Gly Pro Glu Glu Phe Glu Gly Ala Gly Asp Gly Glu
```

```
           1               5              10              15

Pro Pro Glu Asp Asp Ser
      20

(2) INFORMATION FOR SEQ ID NO:84:

(i) SEQUENCE CHARACTERISTICS:
        (A) LENGTH: 23 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:84:

Pro Glu Glu Phe Glu Gly Ala Gly Asp Gly Glu Pro Pro Glu Asp Asp
      1               5                  10                  15

Asp Ser Ala Thr Gly Leu Ala
      20

(2) INFORMATION FOR SEQ ID NO:85:

(i) SEQUENCE CHARACTERISTICS:
        (A) LENGTH: 28 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:85:

Glu His Arg Gly Gly Pro Glu Glu Phe Glu Gly Ala Gly Asp Gly Glu
      1               5                  10                  15

Pro Pro Glu Asp Asp Asp Ser Ala Thr Gly Leu Ala
      20                  25

(2) INFORMATION FOR SEQ ID NO:86:

(i) SEQUENCE CHARACTERISTICS:
        (A) LENGTH: 20 amino acids
        (B) TYPE: amino acid
        (D) TOPOLOGY: linear (ii) MOLECULE TYPE: peptide from HSV-2 glycoprotein G (v) FRAGMENT TYPE: internal (xi) SEQUENCE DESCRIPTION: SEQ ID NO:86:

Ala Pro Pro Pro Glu His Arg Gly Gly Pro Glu Glu Phe Glu Gly
      1               5                  10                  15

Ala Gly Asp Gly
                 20
```

PEPTIDES STRUCTURES AND THEIR USE IN DIAGNOSIS OF HERPES SIMPLEX VIRUS TYPE 2

BACKGROUND OF THE INVENTION

1. Field of the Invention

The invention relates to the diagnosis of herpes simplex virus type 2 (HSV-2) antibodies in samples, especially serum samples, taken from patients suspected of being infected by this virus. The invention provides multiply-displayed peptide structures useful for this purpose and a method and kit for diagnosis using these peptide structures and also monomeric peptides useful for preparation of the multiply-displayed peptides.

2. Description of the Related Art

Herpes simplex virus types 1 and 2 (HSV-1 and HSV-2) are two closely related viruses that infect humans. Most people over age 15 have antibodies to HSV-1 or -2 indicating that they have been infected with and harbour these viruses. Both viruses produce orogenital lesions and can also infect the eye, skin and nervous system. HSV-1 is mainly responsible for oral lesions while HSV-2 is mainly responsible for genital lesions. Following primary infection, the virus can enter a latent state in neurological tissue from which it can periodically reactivate to produce recurrent infections. Reactivations are frequently asymptomatic so that virus can be shed and transmitted in the absence of overt clinical lesions.

The need for a simple and inexpensive serodiagnostic test capable of distinguishing HSV-1 from HSV-2 antibodies was recognised at the WHO recent conference (1996). Serotyping of HSV will be important in trials of HSV vaccines in order to establish the immunological status of individuals before vaccination. It is hoped to prevent neonatal herpes by screening pregnant women and their sexual partners for asymptomatic HSV-2 infections and, where appropriate, recommending precautions designed to prevent transmission.

Progress towards an HSV-2-specific serodiagnostic reagent was facilitated by the identification more than 10 years ago of an HSV-2 glycoprotein, designated 94K or gG2, (Marsden et al, 1978, 1984; Roizman et al., 1984). Subsequently, the HSV-1 counterpart, gG1 was identified. Determination and comparison of the DNA sequence of the genes encoding gG1 and gG2 showed the two proteins to have diverged considerably. The existence of serotype-specific epitopes on gG1 and gG2 (Ackerman et al., 1986; Frame et al., 1986; Marsden et al., 1984, Roizman et al., 1984) raised the possibility of the use of gG1 and gG2 as serotype-specific diagnostic reagents.

Various serological tests for HSV-2 specific antibodies have been developed using gG2. These tests include ELISA, immunodot and western blotting assays, and serum blocking assays using serotype-specific monoclonal antibodies. For these purposes, gG2 has been obtained from a variety of sources including HSV-2 infected mammalian cells, transformed mammalian cells, insect cells infected with recombinant baculoviruses and *Escherichia coli* using several expression vectors. *E. coli* has also been used to express fragments of gG2 containing type-specific regions, and slightly truncated, almost full length fragments of gG2 fused to the maltose binding protein. Antigens from these sources have been used either as crude extracts or following purification by a variety of procedures including ion-exchange, monoclonal antibody-affinity and lectin-affinity chromatography.

Amongst the serological tests using gG2, western blotting is considered the most reliable (WHO conference, Copenhagen, 1995). However, this method is cumbersome, relatively expensive and not suitable for general screening purposes in other than well-equipped diagnostic laboratories. There is a need for a simple, cheap and reliable serodiagnostic test which can be used as an ELISA (Enzyme-Linked ImmunoSorbent Assay) in microtitre plates.

SUMMARY OF THE INVENTION

It has now surprisingly been found that a 16aa (aa=amino acid) peptide, more preferably an 18aa peptide, when subtended as multiple separate branches, each branch containing the peptide sequence, on a core, has a high specificity for HSV-2 antibodies and in particular gives few false positives or false negatives. Consequently, such a peptide structure is valuable in testing for HSV-2 antibodies, especially in samples of body fluid from a patient and most especially in serum samples. The 16aa peptide is that from amino acids 562–577 of gG2 and has the sequence SEQ ID NO: 1 set forth hereinafter. Further, it is possible to include a few additional amino acids at either or both ends of this peptide or to truncate is slightly. The 18aa peptide from amino acids 561–578 of gG2, having SEQ ID NO: 55 set forth hereinafter, is most preferred.

The invention is particularly surprising because this is a region of the HSV-2 glycoprotein gG2 which has high homology with the HSV-1 glycoprotein gG1, McGcoch et al. (1987), yet the peptides of the invention are highly specific for HSV-2 antisera, giving very few false positives with HSV-1 antisera.

In one aspect, the invention provides a multiply-displayed peptide structure of formula (1): $[(X^1)_p$—(16aa sequence)—$(X^2)_q$—Sp$]_n$—core, wherein "16aa sequence" represents a sequence (SEQ ID NO: 68)

Glu Glu Phe Glu Gly Ala Gly Asp Gly Glu Pro Pro
 1               5                    10

Glu Asp Asp Asp
                                             15 and wherein $X^1$ and $X^2$, which may be the same or different, represent from 1 to 6 non-interfering amino acids residues, which may be the same or different residues; Sp represents a spacer group extending outwardly from the core;

n is at least 4;

p is 0 or 1;

q is 0 or 1;

and the linkage between the core and the spacer group may be chemical or physical.

The invention includes the use of the peptide structure of the invention in diagnosis of antibodies to HSV-2. In particular, the invention provides a method of testing for antibodies to herpes simplex virus type 2, in which a binding reaction is performed between the antibodies and a peptide structure of the invention, and the occurrence or extend of binding is detected or measured respectively.

Further, the invention includes a kit for testing the body fluid of a patient for the presence therein of antibodies, comprising (1) a multiply-displayed peptide structure of the invention; and (2) a labelled anti-human immunoglobulin antibody for detection or measurement of binding of the antibodies to the peptide structure.

The invention also includes per se the peptides of formula (2):

$(X^1)_p$—16aa sequence—$(X^2)_z$—$(Sp)_r$, wherein "16aa sequence", $X^1$, $X_2$, p and q are as defined above and r is 0 or 1, and N- and C-terminal functional derivatives thereof.

BRIEF DESCRIPTION OF THE DRAWINGS

FIG. 1 shows detection of HSV-2 and HSV-1 antisera by the method of the invention:

Figure 2:
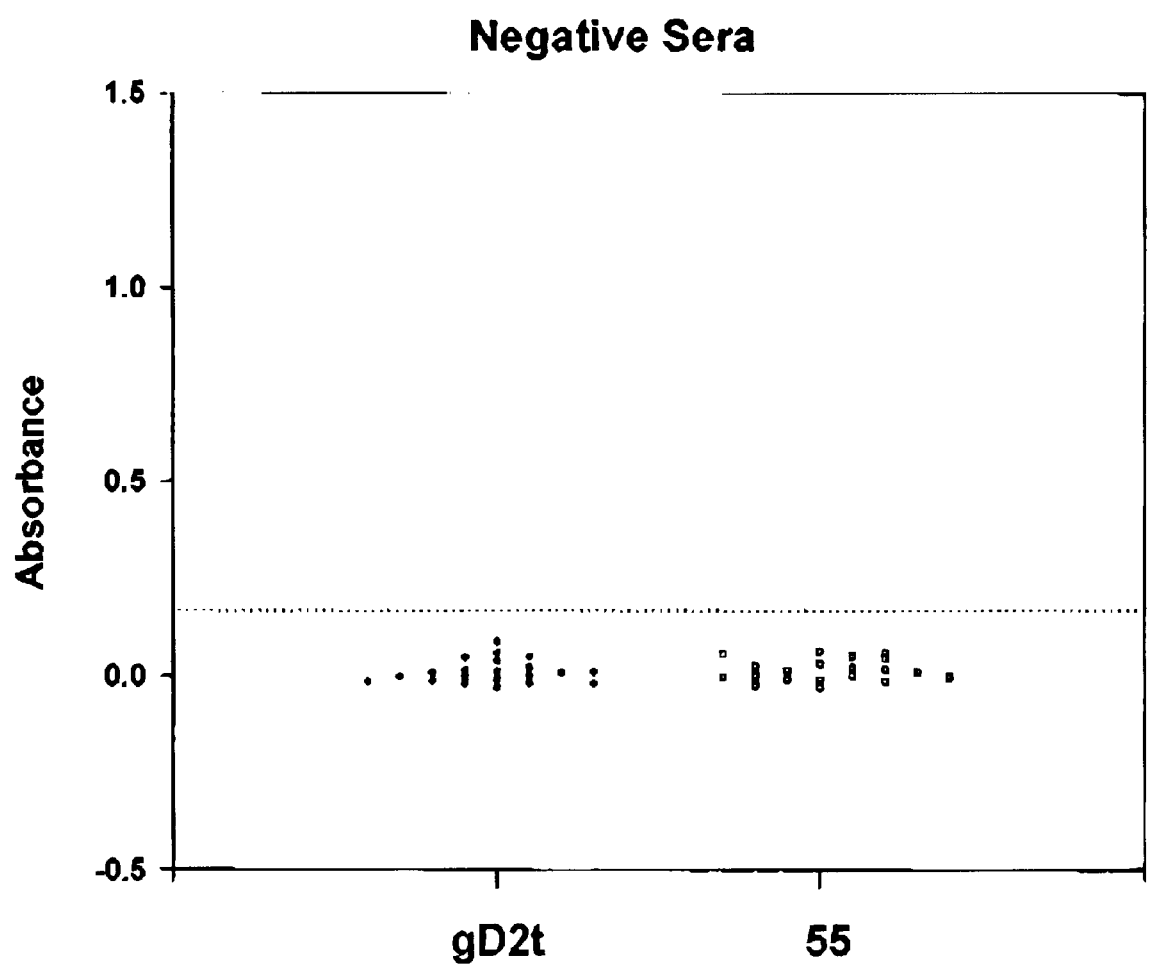

Panels A, C, E—HSV-2; panels B, D and F=HSV 1.

FIG. 2 shows screening by ELISA of sera from individuals not infected with HSV.

DESCRIPTION OF THE PREFERRED EMBODIMENTS

The multiply-displayed peptide structure of the invention is preferably based on a core of branched lysines. Lysine is a dibasic amino acid, providing it with two sites for peptide-bonding. These lysine core structures are well known, having been described by Tam (1988) and Tam et al. (1989), U.S. Pat. No. 5,229,490 (Tam, 1993), European Patent 339,695 (Stichting voor de Technische Wetenschappen) and PCT Publication WO 92/18528 (Medical Research Council). They may be used in this invention. Preferably the structure is all-peptide and of formula (3)

$$[(X^1)_p\text{—16aa sequence—}(X^2)_q\text{—Sp}]_n\text{—}(Lys)_{n-1}\text{—}(X^3)_m \quad (3)$$

wherein n is $2^a$, a being a number from 2 to 5 (i.e. n–4, 8, 16 or 32), the lysine residues denoted by $(Lys)_{n-1}$ being branched, $X^3$ represents from 1 to 4 amino acid residues which may be the same or different, m is 0 or 1, and the other symbols are as defined above. Preferably p is 0 or 1, q is 0 or 1, Sp is a spacer of length equivalent to that of from 4 to 6 glycine residues (and most preferably Sp actually represents from 4 to 6 glycine residues) and m is 0 or 1. Most preferably the peptide structure of the invention is of formula (4):

$$\begin{array}{c}
\text{pepseq-(Gly)}_4 \\
\text{pepseq-(Gly)}_4 \\
\text{pepseq-(Gly)}_4 \\
\text{pepseq-(Gly)}_4
\end{array} \begin{array}{c} \diagdown \\ \diagup \\ \diagdown \\ \diagup \end{array} \begin{array}{c} Lys \\ \\ Lys \end{array} \diagdown \diagup Lys\text{—}X^3 \quad (4)$$

wherein $X^3$ is an amino acid residue, and "pepseq" is the sequence of the peptide $(X^1)_p$— 16aa sequence—$(X^2)_q$, as defined above.

It is not essential to use a branched lysine core. The core can take many forms. It may, for example be a solid inert material onto which the remainder of the molecule is physically absorbed or chemically bonded, normally by covalent bonding. It could be, for example, a linear or branched polymer, including e.g. a polyester of trimethylolpropane or a low molecular weight polyamide or polyacrylamide or a polymer containing dendritic branches, e.g. as in U.S. Pat. No. 4,507,466 (Tomalia et al., 1985). It may be a printed circuit board or array of silicon chips, whereby when the antibody to be tested binds to the peptide structure a change in electrical charge or current occurs, which can be sensed. Preferably linkage to the core is through a covalent bond.

It should be evident from above that is not necessary that the entire molecule of the peptide structure be composed of amino acids. A non-peptide core or non-peptide spacer or non-peptide linkages between one branch and another can be included. However, a wholly peptide or wholly amino acid structure is very convenient from a synthetic view point.

The spacer arm extends outwardly from the core of the structure and comprises any compatible residue. Most preferably the spacer arm molecule comprises residues of amino acids. Preferably, the spacer arm comprises a majority of residues of glycine (which is an uncharged polar amino acid) or non-polar amino acids. The term "non-polar amino acid" as used herein includes alanine, valine, leucine and isoleucine. The preferred length of the spacer arm is at least 4 glycine residues, but even a short spacer, e.g. of length equivalent to a single glycine residue has a small effect. Little advantage is likely in having a length equivalent to more than 6 glycine residues as there may be too much possibility of interference between such highly flexible branches, one with another.

The 16aa sequence SEQ ID NO: 68 can be extended at either its left-hand (N-terminal) or right-hand (C-terminal) end or both with a few amino acid residues which do not interfere with its ability to bind to HSV-2 antibodies with high specificity. These can be those in the "natural" gG2 sequence. Thus, $X^1$ may be Glu His Arg Gly Gly Pro (SEQ ID NO:69), His Arg Gly Gly Pro (SEQ ID NO: 70), Arg Gly Gly Pro (SEQ ID NO: 71), the 3aa sequence Gly Gly Pro, the 2aa sequence Gly Pro or the single aa Pro and $X^2$ ,au be Ser Ala Thr Gly Leu Phe (SEQ ID NO:72), Ser Ala Thr Gly Leu (SEQ ID NO:73), Ser Ala Thr Gly (SEQ ID NO:74), the 3aa sequence Ser Ala Thr, the 2aa sequence Ser Ala or the single aa Ser. $X^1$ and $X^2$ may alternatively comprise other amino acid(s), in which case they are preferably non-polar amino acids or glycine or serine. Most preferably, the 16aa sequence is extended by one amino acid at either or both ends, especially by either or both of the adjacent amino acids of the natural sequence which are an N-terminal Pro and a C-terminal Ser. Thus the following 17aa and 18aa sequences are especially preferred:

```
Pro Glu Glu Phe Glu Gly Ala Gly Asp Gly Glu Pro Pro Glu Asp Asp Asp      (SEQ ID NO: 75)
 1               5                  10                  15

Glu Glu Phe Glu Gly Ala Gly Asp Gly Glu Pro Pro Glu Asp Asp Ser          (SEQ ID NO: 76)
 1               5                  10                  15

Pro Glu Glu Phe Glu Gly Ala Gly Asp Gly Glu Pro Pro Glu Asp Asp Asp Ser. (SEQ ID NO: 55)
 1               5                  10                  15
```

Preliminary results indicate that peptide structures containing the C- or N-terminally extended peptide sequences give slightly less good diagnostic results, in terms of a few more false positives, than "peptide structure 55" containing the 18aa sequence SEQ ID NO: 55.

The peptides from which the peptide sequences are derived and, indeed, the peptide structures themselves if they are wholly peptide, can be made by any of the well known synthetic methods above, but the Fmoc method, especially the continuous flow version, is particularly convenient.

The invention can be practised in any way appropriate to the detection of antibodies, especially on any appropriate fluid, especially a body fluid, likely to contain antibodies.

Although serum is the usual body fluid, other fluids which contain immunoglobulins, e.g. tears, saliva, or milk, could be assayed.

In normal practice, the assay will be carried out heterogeneously by attaching the peptide structure of the invention to an insoluble carrier such as the plastic surface of a microtitre plate, although the invention is not limited to such assays. In a sandwich assay, the antiserum is incubated with the peptide structure for an appropriate period to allow binding and with an antibody to the immunoglobulin. Thus, for example, assuming that the patient is a human and the antibody is of the IgG class, an anti-human IgG antibody, appropriately labelled, is added, the plate is washed and the amount of label bound to the plate (via the antibody and the peptide structure) is measured. The invention can be applied to detecting IgM antibodies, using an anti-human IgM as the second antibody. Alternatively, a competition assay can be performed in which a known amount of labelled antibody is permitted to complete with the serum or to displace it from its binding. Such an assay, however, is less appropriate for detecting small concentrations of antibody. Any of the usual labels, e.g. radiolabels and enzyme labels, can be used, especially peroxidase and alkaline phosphatase. An indirect label, such as biotin, can also be used in conjunction with the appropriate directly labelled binding partner, such as labelled streptavidin or avidin. Radiolabels can be assayed by radioactive counting and enzyme labels by a colorimetric, fluorescent or chemiluminescent signal, for example. An amplification method of detection, such as "Ampak" (Registered Trade Mark) of Nordisk Diagnostics Ltd., which requires an alkaline phosphatase enzyme label, can be used to further sensitise the assay.

The amount of peptide structure to be used per assay, e.g. per well of a plate, will normally be less than 1 μg, preferably less than 0.1 μg and preferably 0.05 to 0.5 μg. The most suitable amount in any particular case will depend on the nature of the peptide structure involved.

In a kit for carrying out the assay, the essential components will in most cases be the peptide structure of the invention and an anti-human immunoglobulin labelled antibody. These are, of course, normally provided in the kit in separate containers.

The invention includes the peptides of formula (2) per se, since they are useful as intermediates in making peptide structures of the invention. For example, it may be convenient to provide peptides lacking a spacer, i.e. in which r is 0, ready for attachment to the remainder of the molecule (core plus spacer). This is particularly helpful when it is more convenient to purchase the core plus spacer from a supplier, especially if the core plus spacer is a non-amino acid polymer containing pendant groups, such as aminoethyl groups, ready to be attached to the C-terminus of the peptide by a peptide linkage. Alternatively the peptides may be synthesised with a spacer [r=1 in formula (2)], ready to attach to a core. The preferred such peptides are as stated above, the 18aa peptide of sequence SEQ ID NO: 55 being the most preferred.

Also included in the invention are derivatives of such peptides, especially having carboxy and amino protecting groups, including particularly peptides in which amino acid side-chains are protected by t-butyloxycarbonyl groups and the N-terminus is protected by 9-fluorenylmethoxycarbonyl (Fmoc). The invention further includes peptides having a "reactive" C-terminal group such as an ester, especially a pentafluorophenyl ester, especially for peptides lacking the spacer (r=0). "Reactive" means capable of reacting with free amino groups of the spacer to form an amide bond therewith. Other such reactive derivatives are well known in the art and included within this invention.

The following Examples illustrate the invention.

EXAMPLES

Materials and Methods

Sera and preliminary serology

A total of 174 serum specimens were collected from 118 individuals. Of these, 155 sera were collected from 100 patients. Paired sera were collected from 55 of these patients. A further 18 sera were collected from 18 children, with a variety of conditions unrelated to HSV. The HSV-specific antibody titres of sera collected in Edinburgh were determined by complement fixation assay (smith et al., 1967), while titres in sera collected in Glasgow were screened using an anti-HSV IgG ELISA kit ("Enzgmost" [Registered Trade Mark], Behring Diagnostics). The HSV-infected patients from whom sera were collected were adults of average age 27 and approximately equal numbers of males and females.

Virus isolation and typing

All virus isolates were obtained from genital lesions with the single exception of one that was isolated from the patient's lip. The viruses were types by indirect fluorescence using a panel of type-specific monoclonal antibodies ("Syva Micro Track" [Registered Trade Mark], Behring Diagnostics).

Synthesis of peptides

A series of 67 peptides, mostly 18aa long overlapping by 10aa, that spanned amino acids 21–699 of the predicted open reading frame of gG2 were synthesised by continuous flow Fmoc chemistry. Residues 1–20 were not synthesised, as these are thought to comprise the signal sequence that is cleaved from the maturing protein. The peptides were made as multiply displayed peptide structures of the invention, each structure consisting of four copies of each amino acid sequence subtended on a branched lysine core (Tam, 1988), but each such amino acid sequence being separated from the core by four glycine residues to increase sensitivity. Such peptide structures can be represented by the formula (5):

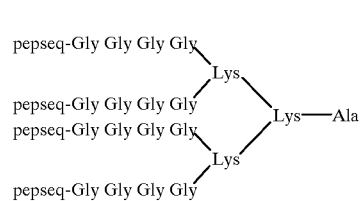

(5)

wherein "pepseq" denotes the same amino acid sequence in each occurrence within the formula and is selected from the sequences of the peptides listed in one letter code in the following Table 1 and having sequence identification numbers 1 to 67. They were made on a Shimadzu PSSM-8 peptide synthesiser using standard Fmoc procedures described by the manufacturer and either HBTU [2-(1H-Benzotriazol-1-yl)-1,1,3,3-tetramethyluronium hexafluorophosphate] or TBTU [2-(1H-Benzotriazol-1-yl)-1,1,3,3-tetramethyluronium tetrafluoroborate] as coupling reagent according to the manufacture's instructions. Peptides were analysed by reverse phase HPLC and were judged to be at least 80% pure.

TABLE 1

Peptides spanning HSV-2 glycoprotein G

| Peptide | Amino acid residues | Sequence of unique region | Peptide | Amino acid residues | Sequence of unique region |
|---|---|---|---|---|---|
| gG2/1 | 21–38 | RGGSGVPGPINPPNSDVV | qG2/35 | 361–378 | KTPLPVSATAMAPSVDPS |
| gG2/2 | 31–48 | NPPNSDVVFPGGSPVAQY | gG2/36 | 371–388 | MAPSVDPSAEPTAPATTT |
| gG2/3 | 41–58 | GGSPVAQYCYAYPRLDDP | gG2/37 | 381–398 | PTAPATTTPPDEMATQAA |
| gG2/4 | 51–68 | AYPRLDDPGPLGSADAGR | gG2/38 | 391–408 | DEMATQAATVAVTPEETA |
| gG2/5 | 61–78 | LGSADAGRQDLPRRVIRH | gG2/39 | 401–418 | AVTPEETAVASPPATASV |
| gG2/6 | 71–88 | LDRRVVRHEPLGRSFLTG | gG2/40 | 411–428 | SPPATASVESSPLPAAAA |
| gG2/7 | 81–98 | LGRSFLTGGLVLLAPPVR | gG2/41 | 421–438 | SPLPAAAAATPGAGHTNT |
| gG2/8 | 91–108 | VLLAPPVRGFGAPNATYA | gG2/42 | 431–448 | PGAGHTNTSSASAAKTPP |
| gG2/9 | 101–118 | GAPNATYAARVTYYRLTR | gG2/43 | 441–458 | ASAAKTPPTTPAPTTPPP |
| gG2/10 | 111–128 | VTYYRLTRACRQPILLRQ | gG2/44 | 451–468 | PAPTTPPPTSTHATPRPT |
| gG2/11 | 121–138 | RQPILLRQYGGCRGGEPP | gG2/45 | 461–478 | THATPRPTTPGPQTTPPG |
| gG2/12 | 131–148 | GCRGGEPPSPKTCGSYTY | gG2/46 | 471–488 | GPQTTPPGPATPGPVGAS |
| gG2/13 | 141–158 | KTCGSYTYTYQGGGPPTR | gG2/47 | 481–498 | TPGPVGASAAPTADSPLT |
| gG2/14 | 151–168 | QGGGPPTRYALVNASLLV | gG2/48 | 491–508 | PTADSPLTASPPATAPGP |
| gG2/15 | 161–178 | LVNASLLVPIWDRAAETF | gG2/49 | 501–518 | PPATAPGPSAANVSVAAT |
| gG2/16 | 171–188 | WDRAAETFEYQIELGGEL | gG2/50 | 511–528 | ANVSVAATTATPGTRGTA |
| gG2/17 | 181–198 | QIELGGELHVGLLWVEVG | gG2/51 | 521–538 | TPGTRGTARTPPTDPKTH |
| gG2/18 | 191–208 | GLLWVEVGGEGPGPTAPP | gG2/52 | 531–548 | PPTDPKTHPHGPADAPPG |
| gG2/19 | 201–218 | GPGPTAPPQAARAEGGPC | gG2/53 | 541–558 | GPADAPPGSPAPPPPEHR |
| gG2/20 | 211–228 | ARAEGGPCVPPVPAGRPW | gG2/54 | 551–568 | APPPPEHRGGPEEFEGAG |
| gG2/21 | 221–238 | PVPAGRPWRSVPPVWYSA | gG2/55 | 561–578 | PEEFEGAGDGEPPEDDDS |
| gG2/22 | 231–248 | VPPVWYSAPNPGFRGLRF | gG2/56 | 571–588 | EPPEDDDSATGLAERTPN |
| gG2/23 | 241–258 | PGFRGLRFRERCLPPQTP | gG2/57 | 581–598 | GLAFRTPNPNKPPPARPG |
| gG2/24 | 251–268 | RCLPPQTPAAPSDLPRVA | gG2/58 | 591–608 | KPPPARPGPIRPTLPPGI |
| gG2/25 | 261–278 | PSDLPRVAFAPQSLLVGI | gG2/59 | 601–618 | RPTLPPGILGPLAPNTPR |
| gG2/26 | 271–288 | PQSLLVGITGRTFIRMAR | qG2/60 | 611–628 | PLAPNTPRPPAQAPAKDM |
| gG2/27 | 281–298 | RTFIRMARPTEDVGVLPP | gG2/61 | 621–638 | AQAPAKDMPSGPTPGHIP |
| gG2/28 | 291–308 | EDVGVLPPHWAPGALDDG | gG2/62 | 631–648 | GPTPQHIPLFWFLTASPA |
| gG2/29 | 301–318 | APGALDDGPYAPFPPRPR | gG2/63 | 641–658 | WFLTASPALDILFITSTT |
| gG2/30 | 311–328 | APFPPRPRFRRALRTDPE | gG2/64 | 651–668 | ILFIISTTLHTAAFVCLV |
| gG2/31 | 321–338 | RALRTDPEGVDPDVRAPR | gG2/65 | 661–678 | TAAFVCLVALAAQLWRGR |
| gG2/32 | 331–348 | DPDVRAPRTGRRLAALTE | qG2/66 | 671–688 | AAQLWRGRAGRRRYAHPS |
| gG2/33 | 341–358 | RRLAALTEDTSSDSPTSA | gG2/67 | 681–699 | RRRYAHPSVRYVCLPPERD |
| gG2/34 | 351–368 | SSDSPTSAPEKTPLPVSA | | | |

EXAMPLE 1

Enzyme-linked immunoabsorbent assay (ELISA)

Sera were tested for reactivity with a truncated version of HSV-2 glycoprotein D (gD2t), as well as peptide structures containing the gG2 peptide sequences. Glycoproteins D of HSV-1 (gD1) and of HSV-2 (gD2) are highly homologous with many epitopes that are recognised by antibodies clicited by both HSV-1 and HSV-2. Glycoprotein D is also an immunodominant protein. These two properties of gD make it a highly sensitive and useful reagent for diagnosis of HSV-specific antibodies. The truncated form contains the first 326 amino acids of gD, but lacks the carboxy-terminal transmembrane domain and is consequently secreted from cells. This property is convenient because the secreted protein can be more easily purified from the cell culture medium than can whole gD from the cell membrane, but does not discriminate between HSV-1 and HSV-2 antibodies. The gD2t, purified to homogenicity, following expression from DNA in Chinese Hamster Ovary cells, was provided by SmithKline Beecham Biologicals (Rixensart, Belgium) at a concentration of 660 μg/ml. It was diluted in phosphate buffered saline (PBS) and used to coat microtitre wells (Immunolon 1, Dynatech) with 0.5 μg or 0.25 μg in 50 μl.

The peptide structures (see Table 1) were dissolved in water whenever possible. Peptide structures not soluble in water were dissolved either in 30% acetic acid (those having the sequences SEQ ID NO: 7, 8, 12, 14, 15, 21, 25, 26, 62) or by bubbling a small volume (<2 ml) of ammonia vapour through the peptide structure water suspension, whereupon the peptide structure formed a clear solution (those having the sequences SEQ ID NO: 16, 17 and 18). Solubilised peptide structures were then diluted in PBS to the concentration indicated in the text and 50 μl added to wells. Both gD2t and the peptide structures were allowed to absorb to the plate at 4° C. overnight. Antigen solution was removed from the plate and unoccupied binding sites on the plate blocked with PBS containing 1% BSA for 1.5 h–2 h. Wells were washed six times with 150 mM NaCl containing 0.05% "Tween 20" ("NaCl-Tween") ("Tween" is a Registered Trade Mark) and were incubated with 50 μl serum, diluted as indicated in the text, for 1.5 h at room temperature on an orbital shaker. The serum was removed and wells were washed a further six times with "NaCl-Tween". For detection of bound antibody, the wells were incubated in turn with 50 μl of biotinylated sheep anti-human 1 gG (Amersham, diluted 1/1000) and 50 μl of streptavidin-conjugated horseradish peroxidase (Amersham, diluted 1/1000), each for 1.5 h at 37° C. followed by six washes with NaCl-"Tween". Chromogenic substrate, o-phenylenediamine dihydrochloride (OPDA), (50 μl) in citrate-phosphate buffer (p114.0) containing 0.01% hydrogen peroxide was added and after 10 minutes, colour development was stopped by addition of 50 μl 2N sulphuric acid. Plates were read on a "Titertek" Multiscan plate reader at 492 nm.

RESULTS

Preliminary screening of all peptides against a subset of the sera

In this initial experiment all of the peptide structures were screened against a set of 24 sera. Four sera were from patients whose isolated virus was found to be type 1 and were antibody-positive, with CF titres ranging from 16 to 256. Fifteen sera were from patients whose isolated virus was found to be type 2 and were antibody-positive, with CF titres ranging from 16 to 256. Three sera were from individuals who had no laboratory evidence of HSV infection in being virus-isolation-and antibody-negative. Two sera were antibody-negative but from patients from whom virus was isolated: HSV-1 was cultured from one of the patients and HSV-2 was cultured form the other. The sera were also screened against gD2t (500 ng per well) to confirm the presence of HSV-specific antibodies. Wells treated with PBS without any antigen served as controls. In this initial screening, wells were coated with 1.0 μg of peptide and the absorbance values at 492 nm were recorded.

For a peptide to be specific for HSV-2, it should have the following properties. It should react with sera containing antibodies elicited by an HSV-2 infection. In addition, the peptide should not react with sera containing no HSV-specific antibodies or with sera containing antibodies elicited by an HSV-1 infection in the absence of an HSV-2 infection.

In the absence of any prior data for the reactivity of the peptides, the data were analysed by two methods. In the first method, a cut-off value of 0.25 was chosen on the basis that it could serve as a suitable value for discriminating between HSV-antibody-positive and negative sera. Only the peptide structures containing the peptide sequences SEQ ID NO: 3, 7, 9, 10, 11, 12, 13, 14, 17, 21, 26, 55, 57, 62, and 66, 67 produced absorbance values of >0.25 with all fifteen HSV-2 sera while only the peptide structures containing the sequences SEQ ID NO: 39, 50, 51, 55, 56, 63 and 64 gave absorbance values of <0.25 with all five antibody-negative sera and only the peptide structures containing the sequences SEQ ID NO: 38, 50 and 55 gave absorbance values of <0.25 with all four HSV-1 sera. Thus, only "peptide structure 55" (having sequence SEQ ID NO: 55) met all of the above-defined criteria required of an HSV-2 antibody-specific reagent. In the second method, the absorbance value of each serum with control, PBS-coated, wells was subtracted from the absorbance values with peptide-coated wells and a cut-off value of 0.1 was chosen. Only the peptide structures containing the sequences SEQ ID NO: 7, 9, 10, 11, 12, 13, 14, 17, 23, 26, 39, 57, 62, 66 and 67 produced absorbance values of >0.1 with all fifteen HSV-2 sera while only the peptide structures containing the sequences SEQ ID NO: 50, 51, 55, 56 and 64 gave absorbance values of <0.1 with all five antibody-negative sera and only the peptide structures containing the sequences SEQ ID NO: 37, 38, 39, 50, 55 and 64 gave absorbance values of <0.1 with all four HSV-1 sera. Thus, none of the peptides met all criteria. However, of the four peptide structures containing sequences SEQ ID NO: 39, 50, 55 and 64 that gave absorbance values of <0.1 with all five antibody-negative and all four HSV-1 sera, peptide structures having the sequences SEQ ID NO: 39, 50 and 64 displayed reactivity with 5, 1 and 4 respectively of 15 HSV-2 sera, while "peptide structure 55" displayed reactivity with 14 of the 15 sera. "Peptide structure 55" was therefore considered a likely candidate for type-specific serodiagnosis of HSV.

EXAMPLE 2

Optimising the amount of peptide and sera to be used

Referring to FIG. 1 of the drawings, wells were coated with four different amounts of peptide structure 55 of the invention: 5 μg (square), 1 μg (diamond, 100 ng (circle) and 10 ng (triangle). Seven sera were diluted 20-fold followed by six further two-fold-dilutions. Wells lacking peptide structure and/or serum served as controls (four square grid). Results for three HSV-2 sera of CF titres 16, 256 and 16 and three HSV-1 sera of CF titres <8, 256 and 16 are shown in FIG. 1 (panels A, C, E—HSV-2; B, D and F=HSV-1. The HSV-2 sera all showed greater reactivity with the wells coated with peptide structure 55, in contrast with the HSV-1 sera which did not react with the peptide structure 55 above the background levels seen with the PBS control. With al four concentration of peptide structure 55 tested, the reactivity of the sera was very similar. A produced an absorbance of greater than 1 when diluted 1:40 or less and appeared to be reaching a plateau. In contrast, both sera C and E showed lower reactivity and the shape of the curves suggested that high reactivities might be achieved with less dilute sera. To investigate whether even lower amounts of peptide could be used, wells were coated with different amounts ranging from 100 ng to 5 pg and tested for reactivity with sera A and E. Below 5 ng per well there was a marked reduction in signal and no response below 100 pg (data not shown).

EXAMPLE 3

Based on these observations, all sera were then screened on wells coated with 100 ng and 10 ng of peptide structure 55 and on wells coated with gD2t: the amount of gD2t was reduced to 250 ng per well to reduce the signal to about that seen with 100 ng of the peptide structure. Sera were tested at dilutions of 5-fold, 10-fold and 20-fold. Wells containing no peptide structure or protein were included for all dilutions of sera.

Establishing cut-off values

The 21 sera that were used as HSV-negative controls comprised 3 from Edinburgh and 18 from Glasgow. They were judged negative by the absence of any clinical symptoms associated with HSV and by their lack of reactivity in ELISA or complement fixation assays (see Methods in Example 1). The sera were diluted 5-fold and screened by ELISA on wells coated with gD2t (250 ng) or peptide structure 55 (either 100 ng or 10 ng) or no antigen (PBS control). The data for gD2t and 100 ng of peptide structure 55 are shown in FIG. 2. A cut-off value of corresponding to the mean plus 5 times the standard deviation (0.166 for gD2t and 0.167 for peptide structure 55) was used for subsequent analysis of other sera and is indicated by the dotted line in the figure.

Analysis of the sera from HSV-positive patients

All sera were screened against wells coated with both 100 ng and 10 ng of peptide 55, 250 ng gD2t and no antigen (PBS control). Most sera were screened at three different dilutions: 5-fold, 10-fold and 20-fold though some sera were screened using only a 5-fold dilution. For each serum, the background absorbance observed without antigen was subtracted from the values obtained for the different antigens. These corrected values constituted the data set.

For analysis, the sera were grouped into 5 classes. Classes 1 and 2 comprised sera that were collected from patients presenting with clinical lesions: class 1 sera had a CF titre of less than 8 while class 2 sera had a CF titre of 8 or greater. Sera comprising classes 3 and 4 were collected between 7 and 20 days (class 3) or greater than 20 days (class 4) after first presentation. Sera in class 5 were from patients who had not presented with a primary lesion and from whom a previous serum had a CF titre of at least 8. Here, primary lesion is defined as a clinically apparent lesion with a CF titre of less than 8 or a CF titre that rises 4-fold within 20 days.

Sera diluted 5-fold and screened on wells coated with 100 ng peptide gave the least number of false negatives. These results are summarised in Table 2 below. A positive result was recorded when the absorbance was above 0.166 (using the means plus 5 times the standard deviation).

TABLE 2

Number of sera scoring positive/ total number tested (%)

| Class of serum (see text) | HSV-1 sera | | HSV-2 sera | |
|---|---|---|---|---|
| | gD2t (comparison) | peptide structure 55 (invention) | gD2t (comparison) | peptide structure 55 (invention) |
| C1 | 3/26 (12) | 0/26 (0) | 4/16 (25) | 2/16 (13) |
| C2 | 1/3 (33) | 0/3 (0) | 11/14 (79) | 6/14 (43) |
| C3 | 24/24 (100) | 0/24 (0) | 15/16 (94) | 13/16 (81) |
| C4 | 8/9 (89) | 0/9 (0) | 13/13 (100) | 12/13 (92) |
| C5 | 9/10 (90) | 0/10 (0) | 22/22 (100) | 22/22 (100) |

Referring to Table 2, peptide structure 55 gave no false positives, with HSV-1 serum. Second, the reactivity of both HSV-1 and HSV-2 sera with gD2t, and HSV-2 sera with peptide structure 55 was lower for those sera taken at the time of first presentation (class 1 and 2 sera), than the reactivity of subsequently sampled sera (class 3, 4 and 5 sera). Overall, 95% of HSV-1 sera (41/43) and 98% of HSV-2 sera (50/51) from classes 3, 4 and 5 reacted with gD2t, while 92% of HSV-2 class 3, 4 and 5 sera (47/51) reacted with peptide structure 55. Third, all (22/22) HSV-2 class 5 sera with both gD2t and peptide structure 55.

Thus, peptide 55 was shown to be completely type-specific for HSV-2 antibodies in human serum, especially for detecting antibodies after an interval of seven days following initial presentation of the clinical lesions.

EXAMPLE 4

Additional peptide structures were synthesised corresponding to extensions at the N- and C-terminus of "peptide structure 55" containing the peptide sequence SEQ ID NO: 55 and made in the 4-branched form of formula (5) above, with the 4-glycine spacer. These were tested, along with gD2t, using the peptide structure or protein at (a) 1 µg or (b) 100 ng per well and in each case with the sera diluted 20-fold. Otherwise the conditions were as in Example 3. Results as shown in Table 3 below. Peptide structure 55 performed the best from the point of view of not giving false positives of HSV-1.

EXAMPLE 5

Two peptide structures of the invention, peptide structure 55 and a peptide structure containing a peptide sequence extended by two aa of the "natural" sequence at each end, were compared with a peptide structure in which the peptide sequence was extended at the N-terminal end but truncated at the C-terminal end by 10aa and 8aa respectively. This comparison shows the criticality of the 16aa core sequence of the present invention. All three peptides were made in the 4-branched, four glycine-spaced form of formula (5). They were all compared with the protein gD2t, as in Example 3, with 100 ng peptide structure or 250 µg protein per well and a 5-fold dilution of the sera. It will be seen that the two peptide structures of the invention performed far better than that having the comparative peptide sequence SEQ ID NO: 86 from all points of view and that the peptide structures of the invention gave no or few false positives of HSV-1.

The following claims define some important aspects of the invention, but do not purport to include every conceivable aspect for which protection might be sought in subsequence continuing and foreign patent applications, and should not be construed as detracting from the generality of the inventive concepts hereinbefore described.

TABLE 3

| | SEQ ID NO. | Sera from individuals not infected with HSV ("blank") | | Sera from individuals | | | |
|---|---|---|---|---|---|---|---|
| | | | | infected with HSV-1 | | infected with HSV-2 | |
| | | 1 µg | 100 ng | 1 µg[a] | 100 ng[b] | 1 µg[c] | 100 ng[d] |
| Total number of sera tested | | 3[e] | 3 | 39 | 40 | 43 | 31 |
| Peptides of formula (5): "pepseq" sequence | | | | | | | |
| PEEFEGAGDGEPPEDDDS("55") | 55 | 0 | 0 | 0 | 0 | 28 | 21 |
| GGPEEFEGAGDGEPPEDDDS | 77 | 1 | 0 | 3 | 2 | 32 | 23 |
| PEEFEGAGDGEPPEDDDSAT | 78 | 0 | 0 | 0 | 0 | 25 | 21 |
| GGPEEFEGAGDGEPPEDDDSAT | 79 | 1 | 0 | 2 | 1 | 33 | 22 |
| HRGGPEEFEGAGDGEPPEDDDS | 80 | 1 | 0 | 2 | 1 | 32 | 22 |
| PEEFEGAGDGEPPEDDDSATGL | 81 | 1 | 0 | 3 | 1 | 32 | 21 |
| HRGGPEEFEGAGDGEPPEDDDSATGL | 82 | 1 | 0 | 3 | 0 | 31 | 22 |
| EHRGGPEEFEGAGDGEPPEDDDS | 83 | 1 | 1 | 4 | 1 | 31 | 22 |
| PEEFEGAGDGEPPEDDDSATGLA | 84 | 1 | 0 | 2 | 2 | 28 | 21 |
| EHRGGPEEFEGAGDGEPPEDDDSATGLA | 85 | 1 | 0 | 5 | 2 | 29 | 22 |
| gD2t (for comparison) | — | 0 | 0 | 24 | 24 | 35 | 25 |

TABLE 4

| | | Sera from individuals | | |
|---|---|---|---|---|
| | SEQ ID NO: | not infected with HSV | infected with HSV-1 | infected with HSV-2 |
| Total number of sera tested | | 3 | 41[a] | 43[b] |
| Peptides of formula (5): "pepseq" sequence | | | | |
| PEEFEGAGDGEPPEDDDS ("55") | 55 | 0 | 0 | 32 |
| GGPEEFEGAGDGEPPEDDDSAT | 79 | 0 | 3 | 33 |
| APPPPEHRGGPEEFEGAGDG (for comparison) | 86 | 1 | 9 | 22 |
| gD2t (for comparison) | — | 0 | 27 | 35 |

[a]15C1, 13C3, 6C4, 7C5. See Ex. 3. The 15 C1 sera gave only 5 reactions out of a total of 60 possible.
[b]9C1, 11C3, 6C4, 17C5. See Ex. 3. The 9 C1 sera gave only 7 reactions out of a total of 36 possible.

Literature References

1. Ackerman, M., Longnecker, R., Roizman, B. and Periera, L. (1986). "Identification, properties and gene location of a novel glycoprotein specified by herpes simplex virus type 1". *Virology,* 150: 207–220.
2. Frame, M. C., Marsden, H. S. and McGeoch, D. J. (1986). "Novel herpes simple virus type 1 glycoproteins identified by antiserum against a synthetic oligopeptide from the predicted product of gene US4". *Journal of General Virology,* 67:745–751.
3. McGeoch, D. J., Moss, H. W., McNab, D. and Frame, M. C. (1987). "DNA Sequence and Genetic Content of the HindIII 1 Region in the Short Unique Component of the Herpes Simplex Virus Type 2 Genome: Identification of the Gene Encoding Glycoprotein G, and Evolutionary Comparison". *Journal of General Virology,* 68: 19–38.
4. Marsden, H. S., Stow, N. D., Preston, V. G., Timbury, M. C. and Wilkie, N. M. (1978). "Physical mapping of herpes simplex virus induced polypeptides". *Journal of Virology,* 28: 624–642.
5. Marsden, H. S., Buckmaster, A., Palfreyman, J. W., Hope, R. G. and Minson, A. C. (1984). "Characterisation of the 92,000-dalton glycoprotein induced by herpes simplex virus type 2." Journal of Virology, 50: 547–554.
6. Roizman, B, Norrild, B., Chan, C. and Percira, L. (1984). "Identification and preliminary mapping with monoclonal antibodies of a herpes simplex virus type 2 glycoprotein lacking a known type-1 counterpart". *Virology,* 133: 242–274.
7. Tam, J. P. (1988). "Synthetic peptide vaccine design: synthesis and properties of a high-density multiple antigenic peptide system". *Proceedings of the National Academy of Sciences USA,* 85: 5409–5413.
8. Tam, J. P. and Zavala, F. (1989). "Multiple antigen peptide: a novel approach to increase detection sensitivity of synthetic peptides in solid-phase immunoassays". *Journal of Immunological Methods,* 124: 53–61.
9. Smith, L. W., Peuthere, J. F. and MacCallam, F. O. (1967). "The incidence of Herpes virus hominis antibody in the population". *J. Hygiene Cambride,* 65: 395–408
10. 'The epidemiology of herpes simplex virus infections and surveillance of other sexually transmitted diseases in Europe', organised by the World Health Organisation (WHO Workshop, 1996).

I claim:

1. A multiply-displayed peptide structure of formula (1):

$$[X^1\text{—16aa sequence—}X^2\text{—Sp}]_n\text{—core},$$

wherein "16aa sequence" represents the sequence:

Glu Glu Phe Glu Gly Ala Gly Asp Gly   (SEQ ID NO:68)
 1               5

Glu Pro Pro Glu Asp Asp Asp;
 10                  15 wherein $S^1$ is Pro and $X^2$ is Ser;

wherein Sp represents a spacer group extending outwardly from the core;

wherein n is at least 4; and wherein the linkage between the core and the spacer group may be chemical or physical.

2. The multiply-displayed peptide structure of claim 1, wherein the linkage between the core and the spacer group is a covalent bond.

3. The multiply-displayed peptide structure of claim 1, which is wholly in the form of a peptide.

4. The multiply-displayed peptide structure of claim 2, which is wholly in the form of a peptide.

5. The multiply-displayed peptide structure of claim 1, wherein the structure is of the formula (4)

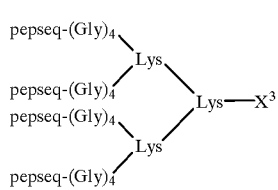
(4)

wherein X³ is an amino acid residue, and "pepseq" is the sequence X¹—16aa peptide—X² as defined in claim 1.

6. The multiply-displayed peptide structure of claim 1, wherein n is from 4 to 16.

7. The multiply-displayed peptide structure of claim 1, wherein the spacer group Sp has a length equivalent to the length of 4 to 6 glycine residues.

8. A method of testing for antibodies to herpes simplex virus type 2, in which a binding reaction is performed between the antibodies and a multiply-displayed peptide structure of claim 1, wherein the occurrence or extent of binding is detected or measured respectively.

9. The method of claim 8, in which the binding reaction is performed as an ELISA.

10. The method of claim 8, wherein the method is carried out on a sample of serum taken from a patient.

11. The method of claim 9, wherein the method is carried out on a sample of serum taken from a patient.

12. A kit for testing the body fluid of a patient for the presence therein of antibodies, comprising (1) a multiply-displayed peptide structure of claim 1 and (2) a labelled anti-human immunoglobulin antibody for detection or measurement of binding of the antibodies to the peptide structure.

13. A peptide of the formula:

```
Pro Glu Glu Phe Glu Gly Ala Gly Asp Gly Glu Pro Pro Glu Asp Asp Asp Ser;    (SEQ ID NO: 55)
 1           5               10              15
``` or an amino or carboxy derivative thereof.

14. The peptide of claim 13 wherein the peptide is linked to a spacer group.

* * * * *